United States Patent [19]

Makino et al.

[11] Patent Number: 5,008,300

[45] Date of Patent: Apr. 16, 1991

[54] VISIBLE LIGHT RAY-CURABLE MONOMERIC COMPOSITION FOR FASTENING LOOSE TEETH

[75] Inventors: Takayuki Makino, Otake; Nobuhiro Mukai, Hiroshima; Hitoshi Ige, Otake, all of Japan

[73] Assignee: Mitsubishi Rayon Company Ltd., Tokyo, Japan

[21] Appl. No.: 405,891

[22] Filed: Sep. 11, 1989

[30] Foreign Application Priority Data

Sep. 16, 1988 [JP] Japan ................................ 63-230062

[51] Int. Cl.$^5$ ........?............ A61K 6/00; C08F 26/06; C08F 226/06
[52] U.S. Cl. .......................................... 522/8; 522/10; 522/167; 522/908; 522/79; 522/83; 523/120; 524/773; 524/847; 526/258
[58] Field of Search ................... 522/8, 10, 121, 908, 522/83, 167, 79

[56] References Cited

U.S. PATENT DOCUMENTS

| | | | |
|---|---|---|---|
| 4,650,845 | 3/1987 | Hegel | 522/68 |
| 4,762,863 | 8/1988 | Sasaki et al. | 522/11 |

FOREIGN PATENT DOCUMENTS 0012535 6/1980 European Pat. Off. .

*Primary Examiner*—Marion E. McCamish
*Assistant Examiner*—Susan Berman
*Attorney, Agent, or Firm*—Finnegan, Henderson, Farabow, Garrett & Dunner

[57] ABSTRACT

A visible light ray-curable monomeric composition for fastening loose teeth, comprising: a filler component consisting of fine, solid particles having an average size of 0.01 to 100 μm and in an amount of 40% to 85% based on the weight of the total weight of the composition; a polyfunctional monomer component consisting of a radical-polymerizable, polyfunctional monomer; a monofunctional monomer consisting of a radical-polymerizable, monofunctional monomer; and a photopolymerization initiator; having a viscosity of 1,000 to 500,000 cps at a temperature of 25° C., and contained in a light-shielded container.

10 Claims, No Drawings

VISIBLE LIGHT RAY-CURABLE MONOMERIC COMPOSITION FOR FASTENING LOOSE TEETH

BACKGROUND OF THE INVENTION

1. Field of the invention

The present invention relates to a visible light ray-curable (hardenable) monomeric composition for fastening loose teeth.

More particularly, the present invention relates to a visible light ray-curable monomeric composition for fastening or fixing loose natural tooth structures to each other or natural tooth structures to dental restoration materials, for example, metallic materials, organic polymeric materials and ceramic materials, with a high adhesion or bonding strength and an aesthetically pleasing appearance.

2. Description of the Related Art

It is known in the field of dentistry that carious tooth structures and defective tooth structures can be restored by using various types of dental restorative materials including metallic materials, for example, gold, silver, platinum, alloy and amalgam materials; organic polymeric materials, for example, polymethylmethacrylate, polycarbonate, cured polyfunctional vinyl polymer, and composite resin materials; and ceramic materials, for example, bore-selenium and other implant materials.

The above-mentioned materials do not have a property of an inherent adhesion to the natural tooth structures, and therefore, many attempts have been made to provide dental adhesion (bonding) agents containing at least one monomeric adhesive compound having a polar radical and capable of adhering dental restoration materials to natural tooth structures therethrough.

Some of the conventional adhering agents can effect the above-mentioned adhesion by curing an adhesive monomeric component in the presence of a redox curing agent (which is a mixture of an organic peroxide compound and an amine compound) or a photopolymerization initiator. Alternatively, other conventional adhering agents can be cured by mixing an adhesive monomeric component with a powdery filler immediately before application thereof, and curing the resultant mixture in the presence of a redox curing agent.

Where a loose tooth structure, e.g., one which is not firmly fixed to an alveolus dentalis due to an alveolitis, for example, pyrrhea alveolaris, is fastened to an adjacent tooth structure, an adhering agent is prepared by mixing and kneading an adhesive monomeric component with a powdery filler comprising an inorganic powder or an organic polymeric powder, outside of the mouth, inserted into gaps between the natural tooth structures, and solidified (hardened) to fix the tooth structures to each other.

Where a tooth structure is fixed to an orthodontic device, for example, a metallic orthodontic device, the adhering agent prepared in the abovementioned manner is inserted into gaps between the tooth structures and the orthodontic device and solidified (cured), and the orthodontic device is further fixed to the tooth structure by a binding wire.

When the conventional adhering agent is practically used, however, the mixing of the monomeric component and the powdery filler must be carried out immediately before the application thereof, and outside of the mouth. Thus, the conventional adhering agent is disadvantageous in that, since the mixture of the monomeric component and the filler is easily hardened (cured) within about 4 to about 7 minutes, the mixing operation must be carried out quickly within a very short time. This rapid mixing operation, however, causes the formation of a number of air bubbles in the resultant adhesive layer, and thus this resultant adhesive layer exhibits a poor mechanical strength.

Usually, a loose tooth structure is spaced from an adjacent tooth structure through a gap having a relatively large thickness, and to fasten the loose tooth structure to the adjacent tooth structure, the gap must be filled with an adhering agent. Namely, the adhering agent must form a thick adhering layer between the tooth structures. To ensure the formation of such a thick adhering layer, the adhering agent must have a high viscosity. It is difficult to obtain a conventional adhering agent consisting of an adhesive monomeric component alone and exhibiting a high viscosity. Also, even if a high viscosity adhering agent can be prepared by mixing a powdery filler into the adhesive monomeric component, it is very difficult to use the resultant adhering agent having a high viscosity in the mouth, and thus such an agent can be employed only by very skilled dentists.

Even if a thick adhering agent layer can be formed from the conventional adhering agent, the resultant thick adhering agent layer exhibits an unsatisfactory poor mechanical strength and surface hardness.

In a liquid-powder mixture type conventional adhering agent, the mixing ratio of the liquid component (adhesive monomeric component) to the powder component (filler) can be varied, but an increase in content of the liquid component results in a lower mechanical strength of the resultant adhering layer, whereas the adhesive strength of the resultant adhering layer to the natural tooth structures or artificial devices is increased. Also, an increase in the powder component content results in a lowered adhesive strength of the resultant adhering agent to the tooth structures or artificial devices, whereas the resultant adhering layer exhibits a high mechanical strength.

Accordingly, there is an urgent need for the provision of a dental adhering agent having a high adhesive strength to natural tooth structures and artificial dental devices and capable of forming an adhering layer having a high mechanical strength.

SUMMARY OF THE INVENTION

An object of the present invention is to provide a visible light ray-curable monomeric composition for fastening loose teeth, which composition comprises a monomeric component, a filler and a curing agent, all premixed together, and can be hardened (cured) by irradiating visible light rays thereto with an easy and simple operation.

Another object of the present invention is to provide a visible light ray-curable monomeric composition for fastening loose teeth, which composition has an enhanced wetting property for the surfaces of natural tooth structures and tooth-restoration material and can finally adhere the natural tooth structures to each other and the natural tooth structure to tooth-restoration materials.

Still another object of the present invention to provide a visible light ray-curable monomeric composition for fastening loose teeth, which composition forms an adhesive layer having an high mechanical strength and an aesthetically pleasing appearance, between the tooth structures or the tooth structures and the tooth-restoration materials.

The above-mentioned objects can be attained by the visible light ray-curable monomeric composition for fastening loose teeth, according to the present invention, which composition comprises
(a) a filler component consisting of at least one type of fine, solid particles having an average size of 0.01 to 100 μm, and in an amount of 40% to 85%, based on the total weight of the monomeric composition;
(b) a polyfunctional monomer component consisting of at least one type of radical polymerizable, polyfunctional monomer;
(c) a monofunctional monomer component consisting of at least one type of radical polymerizable, monofunctional monomer; and
(d) a photopolymerization initiator;
and having a viscosity of 1,000 to 500,000 cps at a temperature of 25° C.

The monomeric composition of the present invention, wherein all the components (a) to (d) are evenly mixed together, is preferably contained in a container, particularly a light-shielded container.

DESCRIPTION OF THE PREFERRED EMBODIMENTS

The adhesive monomeric composition of the present invention can be used (hardened) by irradiation of visible light rays and comprises a filler component (a), a polyfunctional monomer component (b), a monofunctional monomer component (c), and a photopolymerization initiator, all evenly mixed together.

The filler component (a) preferably comprises at least one member selected from the group consisting of inorganic powdery materials, for example, metallic elements of Groups I, II, III, IV and V and transition metal elements, and oxides, hydroxides, halides, sulfates, sulfites, carbonates, phosphates, and silicates of the above-mentioned elements; and organic powdery materials, for example, polymethylmethacrylate, polystyrene, epoxy resin, and polyester resin powders.

Preferable inorganic materials for the filler component (a) are barium sulfate, barium fluoride, silicon dioxide, aluminum oxide, titanium dioxide, quarty and glass powders, glass beads, glass fibers, silica gel, and amorphous silica. Most preferable inorganic materials are a quartz powder and amorphous silica powder.

A preferable organic material for the filler component (a) is a polymethylmethacrylate powder.

The solid particles in the filler component (a) preferably have a size of from 0.1 to 100 μm, more preferably from 0.5 to 30 μm.

In the adhesive monomeric composition of the present invention, the content of the filler component (a) is from 40% to 85%, preferably from 50% to 85%, based on the total weight of the monomeric composition. When the content of the filler component (a) is less than 40%, the resultant adhesive layer exhibits an unsatisfactory mechanical strength. Also, when the content of the filler component (a) is more than 85%, the resultant monomeric composition has an excessively high viscosity and exhibits an unsatisfactory adhesive strength to the tooth structure and artificial restoration devices.

The polyfunctional monomer component (b) usable for the present invention can comprise any polyfunctional monomers usable for conventional dental materials. For example, the polyfunctional monomer component (b) comprises at least one member selected from the group consisting of 2,2-bis[4-(methacryloyloxyethoxy)phenyl]propane; hexafunctional urethane (methacrylate compounds of the formula (I):

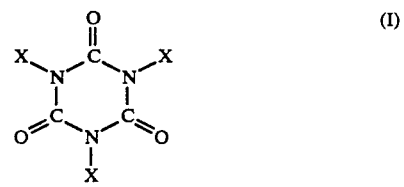

wherein X represents a group of the formula (II):

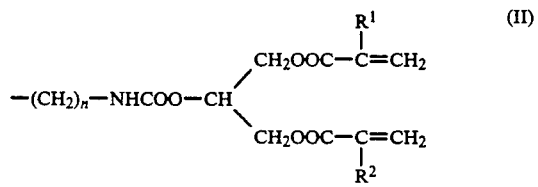

in which n represent an integer of 1 to 10, and $R^1$ and $R^2$ represent, respectively and independently from each other, a member selected from the group consisting of a hydrogen atom and a methyl radical; triethyleneglycol dimethacrylate; 1,6-hexamethyleneglycol dimethacrylate; and 2,2-bis[3-(methacryloyloxy-2-hydroxypropoxyphenyl]propane.

Preferable monomer compounds for the polyfunctional monomer component (b) are 2,2-bis[4-(methacryloyloxyethoxy)phenyl]propane and the monomeric compounds of the formula (I) (u-6HA) wherein n is 6, $R^1$ is a hydrogen atom, and $R^2$ is a methyl radial. Those monomer compounds effectively enhance the mechanical strength of the resultant adhering layer.

The monofunctional monomer component (C) usable for the present inventions comprises at least one member selected from the group consisting of, for example, methylmethacrylate, ethylmethacrylate, 2-hydroxyethylmethacrylate, 2-methacryloyloxyethylphosphate, benzylmethacrylate, glycidylmethacrylate, 2-ethylhexylmethacrylate, styrene, α-methylstyrene, vinyl acetate, methacrylic acid, and acrylic acid.

Preferable monomer compounds for the monofunctional monomer component (c) are 2-hydroxyethylmethacrylate, benzylmethacrylate and 2-methacryloyloxyethylphosphate. Those monomer compounds contribute to the enhancing of the wetting property of the resultant monomeric composition at a surface of a tooth structure or artificial device to be adhered.

In the monomeric composition of the present invention, the content of the monofunctional monomer component (C) is preferably from 1 to 80%, more preferably 5 to 60%, based on the total weight of the polyfunctional and monofunctional monomer components (b) and (c).

Also, the total content of the polyfunctional and monofunctional monomer components (b) and (c) is preferably from 15 to 80%, more preferably 15 to 60%, based on the total weight of the monomeric composition.

The photopolymerization initiator (d) usable for the present invention can comprise any conventional ultraviolet ray-polymerization-initiating compounds, for example, benzophenone, and any conventional visible light ray-polymerization-initiating compounds, but the photopolymerization initiator (d) preferably comprises at least one compound which can initiate the photopolymerization by an irradiation of visible light rays having a wave length of 350 to 1200 nm, which are excluded from a harmful near ultraviolet ray band.

Therefore, the photopolymerization initiator (d) preferably comprises a combination of at least one photosensitizing agent which can be excited by radiation rays having a wave length of 350 to 1200 nm, with at least one reducing agent.

The photosensitizing agent preferably comprises at least one α-diketone compound, for example, camphorquinone, benzil and diacetyl, which exhibit a high photosensitizing activity and thus are useful for the present invention.

In the photopolymerization initiator (d) usable for the present invention, the above-mentioned photosensitizing agent is preferably employed in combination with a reducing agent consisting of at least one tertiary amine compound which effectively enhances the photopolymerization-initiating activity of the photosensitizing agent.

The tertiary amine compound can be selected from the group consisting of aliphatic tertiary amine compounds, for example, trimethylamine, triethylamine, and tripropylamine; and aromatic tertiary amine compounds, for example, isoamyl 4-(N,N-dimethylamino)-benzoate, hexyl 4-(N,N-dimethylamino)benzoate, heptyl 4-(N,N-dimethylamino)benzoate, octyl 4-(N,N-dimethylamino)benzoate, 4,4-bis(dimethylamino)benzophenone, 4,4'-bis(diethylamino)benzophenone, and 4,4'-bis(dibutylamino)benzophenone.

Preferably, the tertiary amine compound is selected from aromatic tertiary amine compounds, more preferably isoamyl 4-(N,N-dimethylamino)benzoate and 4,4'-bis(diethylamino)benzophenone, and those amine compounds are employed preferably in combination with camphorquinone. This combination exhibits an excellent photopolymerization-initiating activity.

In the photopolymerization initiator (d), the amounts of the photosensitizing agent and the reducing agent are variable, depending on the types thereof.

In the combination of camphorquinone with isoamyl 4-(N,N-dimethylamino)benzoate, preferably the camphorquinone is in an amount of 0.01% to 25%, more preferably 0.05% to 15%, and the isoamyl 4-(N,N-dimethylamino)benzoate is in an amount of 0.05% to 30%, more preferably 0.1% to 25%, based on the total weight of the polyfunctional and monofunctional monomer components (b) and (c).

Also, in the combination of camphorquinone with 4,4'-bis(diethylamino)benzophenone, preferably the camphorquinone is in an amount of from 0.005% to 30%, more preferably 0.03% to 20%, and the 4,4'-bis(diethylamino)benzophenone is in an amount of from 0.01% to 25%, more preferably 0.05% to 20%, based on the total weight of the polyfunctional and monofunctional monomer components (b) and (c).

To harden the monomeric composition of the present invention in a short time, visible light ray irradiation sources able to generate and irradiate visible light rays having a wave length of from 350 to 1200 nm, for example, a halogen arc lamp, xenon arc lamp, mercury arc lamp, and luminescent discharge lamp, are preferably utilized.

To the adhesive monomeric composition of the present invention is optionally added at least one member selected from a polymerization inhibitors comprising at least one member selected from, for example, hydroquinone, methoxybenzophenone, methylphenol, and hydroquinonemonomethylether; antioxidants; ultraviolet absorbing agents, for example, benzophenone; pigments, for example, iron oxides and titanium dioxide; and dyes, if necessary.

The adhesive monomeric composition of the present invention has a viscosity of 1,000 to 500,000 cps, preferably 5,000 to 400,000 cps, at a temperature of 25° C. The viscosity can be controlled by controlling the type and content of the filler component (a).

If the viscosity is less than 1.000 cps or more than 500,000 cps, the resultant monomeric composition exhibits a poor handling property.

In the adhesive monomeric composition of the present invention, all of the components (a), (b), (c) and (d) must be evenly mixed together, and the mixture is preferably contained in one container. The container is shielded from the entry of light therein. There is no limitation to the shape and size of the container, but the container must be able to directly and easily feed the monomeric composition to a tooth structure to be treated. Therefore, the container is preferably compressible or capacity-variable and has a sealable feed opening having an inside diameter of 1 mm to 5 mm.

The compressible or capacity-variable container can be a selected from containers, for example, tubes, cylinders, bags and bottles, in which at least a portion of the container wall is made of a flexible or elastic material and which ca be easily compressed by the fingers to reduce the inside capacity thereof; and other containers, for example, a cylinder or bottle, having a movable bottom which can be moved toward the inside of the container to push the content in the container toward the feed opening of the container.

Note, the container for containing the monomeric composition of the present invention is not limited to the above-exemplified containers.

In the conventional adhesive monomeric compositions for fixing natural tooth structures to each other or a natural tooth structure to an artificial restoration device, two or more components must be mixed outside the mouth immediately before applying the composition.

The monomeric composition of the present invention, however, does not require this premixing operation and can be directly applied to an object to be fixed, and is easily hardened by irradiating harmless visible light rays thereto.

EXAMPLES

The present invention will be further illustrated by way of specific examples, which are representative and do not restrict the scope of the present invention in any way.

In the examples, the adhering property and adhesive strength of a monomeric composition were tested in the following manner.

(1) A fresh cattle anterior tooth was cut by a precision cutter (available under a trademark of Isomet, from Bühler Co) immediately after extraction to expose a fresh enamel surface, and the exposed enamel surface was polished with a water-proof abrasive paper (JIS, No. 1000) under a flow of water.

(2) The polished enamel surface was treated with a phosphoric acid type etching agent (made by GC Dental Industry Co.), washed with water, and then air-dried.

(3) A circular cylinder-shaped silicon ring having an inside diameter of about 5 mm, a height of about 5 mm and a thickness of about 3 mm (and able to be opened at one side) was placed on the enamel surface, and the inside space of the silicone ring was filled with a monomeric composition.

(4) A visible light-irradiation apparatus (available under the trademark (G.C. Light, from GC Dental Industry Co.) was arranged in such a manner that a irradiating opening of the apparatus was close to the upper face of the monomeric composition-filled silicone ring, the visible light was irradiated toward the monomeric composition for 60 seconds to cure (harden) the monomeric composition, the monomeric composition-filled silicon ring was then left to stand for 60 seconds to cure (harden) the monomeric composition, and the monomeric composition-filled silicone ring was then left to stand for about 10 minutes. Then the silicone ring was removed from the resultant adhesive resinous layer to provide a tooth test piece with an adhesive resinous layer.

(5) The test piece was stored in water at a temperature of 37° C. for a predetermined time, and then a bar consisting of a methylmethacrylate resin and having the same diameter as that of the adhesive resinous layer was adhered to the adhesive resinous layer by a high-speed polymerizing resin (available under the trademark Uni First, from GC Dental Industry Co.).

(6) The resultant test piece was subjected to a tensile test under the following conditions, to measure the adhering strength.

Tensilometer: Tensilon (Trademark of Toyo Baldwin Co.)
Speed of cross head (Stretching speed): 0.5 mm/min
Speed of chart: 10 mm/min
Full scale: 20 kgw (7) Flexural strength test A stainless steel frame-shaped mold having a length of 30 mm, a width of 2 mm, and a height (thickness) of 2 mm was placed on a horizontal glass plate, filled with an adhesive monomeric composition, and covered by a horizontal glass plate.

The visible light irradiation apparatus was arranged so that the light irradiating opening of the apparatus was spaced 1 mm from the covering glass plate, and the light was irradiated to the adhesive monomeric composition through the covering glass plate for seconds. The same procedures as mentioned above were carried out through the bottom glass plate. The resultant hardened resinous test piece was immersed in water at a temperature of 37° C. for 24 hours, and then subjected to a flexural strength test under the following conditions.

Tester: Bending tester (trademark: IS-500, made by Shimazu Seisakusho)
Speed of cross head: 1.0 mm/min
Speed of chart: 200 mm/min
Span length: 20 mm
Full scale: 10 kgw (8) Viscosity measurement A viscosity of the adhesive monomeric composition was measured at a temperature of 25° C. in a constant temperature vessel by using a B-type viscometer (type: B8R, made by Tokyo Keiki K.K.)

EXAMPLES 1 to 8

Preparation of monomeric compositions L-1 to L-8

In Examples 1 to 8, 8 different monomeric compositions L-1 to L-8 were prepared by evenly mixing the filler component (a), the polyfunctional monomer component (b), the monofunctional monomer component (c) and the photopolymerization initiator (d), each consisting of the compounds in the amounts as shown in Table 1, in a dark room using a universal mixer.

The resultant compositions exhibited the viscosities at a temperature of 25° C. as shown in Table 1.

Each of the monomeric compositions L-1 to L-8 was charged in an amount of 3 g in a light-shielded flexible cylinder consisting of a polyethylene resin and having a length of 6 cm and provided with a top opening having an inside diameter of 0.3 cm, and the top opening was closed by a cap. The sealed cylinder was then stored in a thermostatic room at a temperature of 25° C. for 3 months. Thereafter, the viscosity of the stored monomeric composition was measured to establish the stability of the monomeric composition during storage. The results are shown in Table 1.

Table 1 clearly indicates that all of the monomeric compositions L-1 to L-8 of the present invention exhibited an excellent stability during storage.

TABLE 1

| | Item | | | | | | | | | |
|---|---|---|---|---|---|---|---|---|---|---|
| | Filler component (a) (g) | | | Polyfunctional monomer component (b) (g) | | | | Monofunctional monomer component (c) (g) | | |
| Composition | Quartz powder (*)1 | Amorphous silica (*)2 | PMMA powder (*)3 | u-6HA (*)4 | Bis-MEPP (*)5 | Bis-GMA (*)6 | 3G (*)7 | HEMA (*)8 | BMA (*)9 | MMA (*)10 |
| L-1 | 64 | 16 | — | 12 | 3 | — | — | 5 | — | — |
| L-2 | 56 | 14 | — | 18 | 5 | — | — | 7 | — | — |
| L-3 | 48 | 12 | — | 25 | 10 | — | — | — | 5 | — |
| L-4 | 56 | 14 | — | 10 | 10 | — | — | — | 10 | — |
| L-5 | 56 | 14 | — | 5 | 15 | — | 5 | 5 | — | — |
| L-6 | 56 | 14 | — | 20 | — | 5 | — | — | 5 | — |
| L-7 | 56 | — | 14 | — | — | 20 | 5 | 5 | — | — |
| L-8 | 56 | — | 14 | — | 20 | — | — | — | 5 | 5 |

| | Item | | | | |
|---|---|---|---|---|---|
| | Photopolymerization initiator (d) (g) | | Content of filler component (a) (%) (a)/(a) + (b) + (c) | Viscosity at 25° C. (cps) | |
| Composition | Camphor-quinone | EAB (*)11 | | Initial | After 3 months storage |
| L-1 | 0.4 | 2.0 | 80 | 354,000 | 352,000 |
| L-2 | 0.4 | 2.0 | 70 | 280,000 | 275,000 |

TABLE 1-continued

| | | | | | |
|---|---|---|---|---|---|
| L-3 | 0.4 | 2.0 | 60 | 150,000 | 141,000 |
| L-4 | 0.4 | 2.0 | 70 | 250,000 | 256,000 |
| L-5 | 0.4 | 2.0 | 70 | 234,000 | 230,000 |
| L-6 | 0.4 | 2.0 | 70 | 310,000 | 317,000 |
| L-7 | 0.4 | 2.0 | 70 | 217,000 | 210,000 |
| L-8 | 0.4 | 2.0 | 70 | 198,000 | 201,000 |

Note:
(*)1 Average size = about 4 μm
(*)2 Trademark = Aerosil R-972, made by Degussa Co., hydrophobic amorphous silica particles, average size = 0.04 μm
(*)3 Polymethylmethacrylate powder, average size = about 20 μm
(*)4 Hexafunctional urethane acrylate compound of the formula (I)
(*)5 2,2-Bis[4-(methacryloyloxyethoxy)phenyl]propane
(*)6 2,2-Bis[4-(3-methacryloyloxy-2-hydroxypropoxy)phenyl]propane
(*)7 Triethyleneglycol dimethacrylate
(*)8 2-Hydroxyethyl methacrylate
(*)9 Benzyl methacrylate
(*)10 Methyl methacrylate
(*)11 4,4'-bis(diethylamino)benzophenone Adhering strength test and flexural strength test In each of Examples 1 to 8, the adhesive monomeric composition as indicated in Table 2 was subjected to a test of the adhering strength thereof to an enamel surface of a cattle tooth and a flexural strength test of the cured resinous test pieces in the manner mentioned above.

The results are shown in Table 2.

Adhering strength test

In each of comparative Examples 1 to 4, the comparative monomeric composition as indicated in Table 4 was subjected to the adhering strength test in the manner described above.

The results are shown in Table 4.

TABLE 2

| | | Item | |
|---|---|---|---|
| Example No. | Type of adhesive monomeric composition | Average adhering strength (kg/cm²) (*)12 after one day storage in water at 37° C. | Average flexural strength (kg/cm²) (*)12 after one day storage in water at 37° C. |
| 1 | L-1 | 124.8 | 1050 |
| 2 | L-2 | 139.2 | 1010 |
| 3 | L-3 | 132.1 | 950 |
| 4 | L-4 | 145.0 | 1250 |
| 5 | L-5 | 118.7 | 1140 |
| 6 | L-6 | 121.9 | 1180 |
| 7 | L-7 | 97.5 | 980 |
| 8 | L-8 | 86.3 | 920 |

(*)12 ... An average value from 5 test pieces

COMPARATIVE EXAMPLES 1 to 4

Preparation of comparative adhering monomeric compositions L-9 to L-12

In comparative Examples 1 to 4, four different comparative adhering monomeric compositions L-9 to L-12 of a filler component (a), a polyfunctional monomer component (b), and a photopolymerization initiator (d), each consisting of the compounds in the amounts as shown in Table 3, were tested in the same manner as in Example 1.

The viscosities of the resultant compositions are shown in Table 3.

| | | Item |
|---|---|---|
| Example No. | Type of adhesive monomeric composition | Average adhering strength (kg/cm²) after one day storage in water at 37° C. |
| Comparative Example 1 | L-9 | 57.8 |
| Comparative Example 1 | L-10 | 31.4 |
| Comparative Example 1 | L-11 | 50.2 |
| Comparative Example 1 | L-12 | 45.6 |

TABLE 3

| | Item | | | | | | | | | |
|---|---|---|---|---|---|---|---|---|---|---|
| | Filler component (a) (g) | | | Polyfunctional monomer component (b) (g) | | | | Photopolymerization initiator (d) (g) | | Content of filler component (a) (%) (a)/(a) + (b) | Initial viscosity at 25° C. (CPS) |
| Composition | Quartz powder | Amorphous silica | PMMA powder | 6-6HA | Bis-MEPP | Bis-GMA | 3G | Camphorquinone | EAB | | |
| L-9 | 56 | 14 | — | 10 | 10 | — | 10 | 0.4 | 2.0 | 70 | 345,000 |
| L-10 | 56 | — | 14 | 10 | 10 | — | 10 | 0.4 | 2.0 | 70 | 290,000 |
| L-11 | 56 | 14 | — | 10 | 10 | 10 | 10 | 0.4 | 2.0 | 70 | 350,000 |
| L-12 | 56 | 14 | — | 5 | 5 | — | 5 | 0.4 | 2.0 | 70 | 370,000 |

COMPARATIVE EXAMPLES 5 to 10

Preparation of comparative adhesive monomeric compositions L-13 to L-18

In Comparative Examples 5 to 10, six different comparative monomeric compositions L-13 to 18 were prepared from a filler composition (a), polyfunctional and monofunctional monomer components (b) and (c), and a photopolymerization initiator (d), each consisting of the compounds in the amounts indicated in Table 5, in the same manner as in Example 1.

Adhering strength test and flexural strength test

The comparative compositions L-13 to L-18 were subjected to the adhering strength test and the comparative compositions L-13 to L-17 were subjected to the flexural strength test, in the above-described manner. The results are shown in Table 6.

TABLE 6

| Example No. | Type of adhesive monomeric composition | Average adhering strength (kg/cm$^2$) after one day storage in water at 37° C. | Average flexural strength (kg/cm$^2$) after one day storage in water at 37° C. |
| --- | --- | --- | --- |
| Comparative Example 5 | L-13 | 72.3 | 430 |
| Comparative Example 6 | L-14 | 46.6 | 480 |
| Comparative Example 7 | L-15 | 35.0 | 360 |
| Comparative Example 8 | L-16 | 28.4 | 290 |
| Comparative Example 9 | L-17 | 23.5 | 250 |
| Comparative Example 10 | L-18 | 0.0 | — |

EXAMPLES 9 to 18

In Examples 9 to 18, ten different adhesive monomeric compositions L-19 to L-28 were prepared, in the composition shown in Table 7, in the same manner as in Example 1. The resultant compositions exhibited the viscosities shown in Table 7.

TABLE 5

| Composition | Filler component (a) (g) | | | Polyfunctional monomer component (b) (g) | | | | Monofunctional monomer component (c) (g) | | |
| --- | --- | --- | --- | --- | --- | --- | --- | --- | --- | --- |
| | Quartz powder | Amphorous silica | PMMA powder | u-6HA | Bis-MEPP | Bis-GMA | 3G | HEMA | BMA | MMA |
| L-13 | 20 | 5 | 5 | 30 | 20 | — | 15 | 5 | — | — |
| L-14 | 13 | 7 | — | 20 | 20 | 20 | — | 15 | 5 | — |
| L-15 | 5 | 5 | — | 20 | 40 | 10 | 10 | — | 10 | — |
| L-16 | — | 4 | 1 | 30 | 10 | 30 | — | 5 | 10 | 10 |
| L-17 | — | — | — | 60 | 10 | 10 | — | 10 | 10 | — |
| L-18 | 80 | 7 | — | 8 | 2 | — | — | — | 3 | — |

| Composition | Photopolymerization initiator (d) (g) | | Content of filler component (a) (%) (a)/(a) + (b) + (c) | Initial viscosity at 25° C. (cps) |
| --- | --- | --- | --- | --- |
| | Camphorquinone | EAB | | |
| L-13 | 0.4 | 2.0 | 30 | 4,800 |
| L-14 | 0.4 | 2.0 | 20 | 3,500 |
| L-15 | 0.4 | 2.0 | 10 | 2,800 |
| L-16 | 0.4 | 2.0 | 5 | 2,000 |
| L-17 | 0.4 | 2.0 | 0 | 600 |
| L-18 | 0.4 | 2.0 | 87 | 700,000 |

TABLE 7

| Composition | Filler component (a) (g) | | | Polyfunctional monomer component (b) (g) | | | | Monofunctional component (c) (g) | |
| --- | --- | --- | --- | --- | --- | --- | --- | --- | --- |
| | Quartz powder | Amorphous silica | PMMA powder | u-6HA | Bis-MEPP | Bis-GMA | 3G | HEMA | BMA |
| L-19 | 64 | 16 | — | 12 | 3 | — | — | 5 | — |
| L-20 | 56 | 14 | — | 18 | 5 | — | — | 7 | — |
| L-21 | 56 | 14 | — | 10 | 10 | — | — | — | 10 |
| L-22 | 56 | — | 14 | 5 | 15 | — | 5 | 5 | — |
| L-23 | 56 | — | 14 | 20 | — | 5 | — | — | — |
| L-24 | 64 | 16 | — | 12 | 3 | — | — | — | — |
| L-25 | 56 | 14 | — | 18 | 5 | — | — | — | — |
| L-26 | 56 | 14 | — | 20 | 5 | — | — | 2 | — |
| L-27 | 56 | — | 14 | — | — | 20 | 5 | — | — |

TABLE 7-continued

| L-28 | 56 | — | 14 | — | 20 | — | 5 | — | — |

| | Monofunctional component (c) (g) | | | Photopolymerization initiator (d) (g) | | | Content of filler component (a) (%) | Initial viscosity |
|---|---|---|---|---|---|---|---|---|
| Composition | MOEMA (*)13 | MMA | GMA (*)14 | Camphor-quinone | DAB (*)15 | EAB | (a)/(a) + (b) + (c) | at 25° C. (cps) |
| L-19 | — | — | — | 0.4 | 2.0 | — | 80 | 335,000 |
| L-20 | — | — | — | 0.4 | 2.0 | — | 70 | 290,000 |
| L-21 | — | — | — | 0.4 | 2.0 | — | 70 | 265,000 |
| L-22 | — | — | — | 0.4 | 2.0 | — | 70 | 283,000 |
| L-23 | — | 5 | — | 0.4 | 2.0 | — | 70 | 241,000 |
| L-24 | 5 | — | — | 0.4 | — | 2.0 | 80 | 370,000 |
| L-25 | — | — | 5 | 0.4 | — | 2.0 | 70 | 310,000 |
| L-26 | — | — | 3 | 0.4 | — | 2.0 | 70 | 273,000 |
| L-27 | 5 | — | — | 0.4 | — | 2.0 | 70 | 266,000 |
| L-28 | 5 | — | — | 0.4 | — | 2.0 | 70 | 277,000 |

Note:
(*)13 2-Methacryloyloxymethyl methacrylate
(*)14 Glycidyl methacrylate
(*)15 Isoamyl (N,N-dimethylamino)benzoate Adhering strength test and flexural strength test The compositions L-19 to L-28 were subjected to the adhering strength test and the flexural strength test. The results are shown in Table 8.

TABLE 8

| Example No. | Type of adhesive monomeric composition | Average adhering strength (kg/cm$^2$) after one day storage in water at 37° C. | Average flexural strength (kg/cm$^2$) after one day storage in water at 37° C. |
|---|---|---|---|
| 9 | L-19 | 127.8 | 1050 |
| 10 | L-20 | 137.5 | 1120 |
| 11 | L-21 | 129.4 | 1270 |
| 12 | L-22 | 105.7 | 850 |
| 13 | L-23 | 95.4 | 970 |
| 14 | L-24 | 130.5 | 1140 |
| 15 | L-25 | 138.0 | 1210 |
| 16 | L-26 | 121.5 | 1070 |
| 17 | L-27 | 101.6 | 810 |
| 18 | L-28 | 107.6 | 930 |

We claim:

1. A visible light ray-curable monomeric dental adhesion composition consisting essentially of:

(a) a filler component consisting of at least one type of fine, solid particles having an average size of from 0.01 to 100 μm and in an amount of from 40% to 85% base on the total weight of the monomeric composition;

(b) a polyfunctional monomer component consisting of at least one type of radical polymerizable, polyfunctional monomer selected from the group consisting of 2,2-bis[4(methacryloxyethoxy)phenyl]-propane and a hexafunctional urethane acrylate compound of the formula:

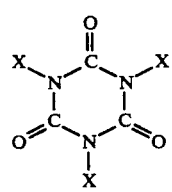

wherein X is a group of the formula:

$$-(CH_2)_n-NHCOO-CH\begin{matrix}CH_2OOC-C(R^1)=CH_2\\ CH_2OOC-C(R^2)=CH_2\end{matrix}$$

n is an integer of 1 to 10, and $R^1$ and $R^2$ are each selected from the group consisting of a hydrogen atom and a methyl radical;

(c) a monofunctional monomer component comprising at least one type of radical polymerizable, monofunctional monomer selected from the group consisting of 2-hydroxyethyl methacrylate, 2-methacryloyloxyethyl phosphate, benzyl methacrylate, and 2-ethylhexyl methacrylate;

the monofunctional monomer component (c) being present in an amount of from 1% to 80% based on the total weight of the polyfunctional monomer component (b) and the monofunctional monomer component (c), and the polyfunctional monomer component (b) and the monofunctional monomer component (c) being present in a total amount of from 15% to 80% based on the total weight of the monomeric composition; and (d) a photopolymerization initiator; said monomeric composition having a viscosity of 1,000 to 500,000 cps at a temperature of 25° C.

2. The monomeric composition as claimed in claim 1 wherein the filler (a) comprises at least one member selected from the group consisting of quartz powder, amorphous silica powder, and polymethylmethacrylate resin powder.

3. The monomeric composition as claimed in claim 1, wherein the photopolymerization initiator (d) comprises a combination of at least one photosensitizing agent which can be excited by radiation rays having a wave length of 350 to 1200 nm, with at least one reducing agent.

4. The monomeric composition as claimed in claim 3, wherein the photosensitizing agent comprises an α-diketone compound.

5. The monomeric composition as claimed in claim 4, wherein the α-diketone compound is selected from the group consisting of camphorquinone, benzil and diacetyl.

6. The monomeric composition as claimed in claim 3, wherein the reducing agent comprises at least one tertiary amine.

7. The monomeric composition as claimed in claim 6, wherein the tertiary amine is an aromatic tertiary amine.

8. The monomeric composition as claimed in claim 7, wherein the aromatic tertiary amine is selected from the group consisting of isoamyl 4-(N,N-dimethylamino)benzoate, hexyl 4-(N,N-dimethylamino)benzoate, heptyl 4-(N,N-dimethylamino)benzoate, octyl 4-(N,N-dimethylamino)benzoate, 4,4'-bis(dimethylamino)benzophenone, 4,4'-bis(diethylamino)benzophenone, and 4,4'-bis(dibutylamino)benzophenone.

9. The monomeric composition as claimed in claim 1, wherein the photopolymerization initiator comprises 0.01 to 25% of camphorquinone and 0.05 to 30% of isoamyl 4-(N,N-dimethylamino)benzoate, based on the total weight of the polyfunctional and monofunctional monomer components (b) and (c).

10. The monomeric composition as claimed in claim 1, wherein the photopolymerization initiator comprises 0.005 to 30% of camphorquinone and 0.01 to 25% of 4,4'-bis(diethylamino)benzophenone.

* * * * *

UNITED STATES PATENT AND TRADEMARK OFFICE
CERTIFICATE OF CORRECTION

PATENT NO. : 5,008,300

DATED : April 16, 1991

INVENTOR(S) : Takayuki Makino et al.

It is certified that error appears in the above-identified patent and that said Letters Patent is hereby corrected as shown below:

Claim 1, column 13, line 51, change "base" to --based--; and column 14, line 24, the formula should appear within the text of claim 1.

Signed and Sealed this

Eighth Day of September, 1992

*Attest:*

DOUGLAS B. COMER

*Attesting Officer* — *Acting Commissioner of Patents and Trademarks*